United States Patent [19]
Wool

[11] Patent Number: 5,174,753
[45] Date of Patent: Dec. 29, 1992

[54] ORTHODONTIC ARCH WIRE HAVING A NON-SYMMETRICAL TRAPEZOIDAL CROSS-SECTION

[76] Inventor: Arthur L. Wool, Faust Rd., Box 210J, Sinking Spring, Pa. 19608

[21] Appl. No.: 556,566

[22] Filed: Jul. 24, 1990

[51] Int. Cl.⁵ .............................................. A61C 3/00
[52] U.S. Cl. ........................................ 433/8; 433/20
[58] Field of Search ..................... 433/8, 9, 10, 11, 12, 433/13, 14, 15, 16, 17, 20

[56] References Cited

U.S. PATENT DOCUMENTS

| | | | |
|---|---|---|---|
| 3,193,930 | 7/1965 | Bien | 433/15 |
| 4,248,588 | 2/1981 | Hanson | 433/11 |
| 4,386,909 | 6/1983 | Hanson | 433/20 |
| 4,424,033 | 1/1984 | Wool | 433/20 |
| 4,793,804 | 12/1988 | Schudy | 433/8 |
| 4,850,865 | 7/1989 | Napolitano | 433/20 |
| 4,897,036 | 1/1990 | Kesling | 433/20 |

Primary Examiner—John J. Wilson
Attorney, Agent, or Firm—Antonelli, Terry, Stout & Kraus

[57] ABSTRACT

An orthodontic appliance including a series of orthodontic brackets configured to be secured to the teeth of patient, the brackets having slots for supporting an orthodontic arch wire, and an orthodontic arch wire extending through the slots. The orthodontic arch wire is arch-shaped and includes posterior segments and an anterior segment connecting the posterior segments. Either the anterior segment, or the entire arch wire, has a non-symmetrical, trapezoidal cross-section, and can be supported by bracket slots having either a rectangular or non-symmetrical trapezoidal shape.

15 Claims, 4 Drawing Sheets

ORTHODONTIC ARCH WIRE HAVING A NON-SYMMETRICAL TRAPEZOIDAL CROSS-SECTION

BACKGROUND OF THE INVENTION

The present invention relates to orthodontic appliances for correcting misalignments of a patient's teeth. More particularly, the present invention relates to an orthodontic arch wire which can be used together with a series of orthodontic brackets in order to provide efficient and effective correction of a variety of classes of malocclusions.

A variety of malocclusions can be corrected through the use of orthodontic arch wires. In corrections using arch wires, brackets are secured to the patient's teeth by the use of bands to which the brackets are welded, or by cementing brackets directly to the teeth. Typically, in each of a number of stages during the course of treatment, an arch wire is secured in the brackets. As treatment progresses, the arch wire which is used more closely approaches the ideal arch form. The arch wires progressively correct misalignments of the patient's teeth.

Malocclusions have conventionally been corrected through what is known in the art as edgewise or light wire techniques. In the edgewise technique, which is utilized to avoid the problem of "tipping" and to prevent the teeth from acquiring a "dished" appearance, orthodontic brackets having open rectangular slots are secured to the patient's teeth, and an orthodontic arch wire having a rectangular cross-section is inserted into the rectangular slots so that such slots support the arch wire. Since the arch wire cannot rotate in the rectangular slots of the brackets, and since the brackets are fixed to the incisors, rearwardly applied forces on the arch wire are prevented from causing "tipping" of the incisors. The non-rotating relationship between the rectangular arch wire and the bracket is such that torque can be applied to the teeth by the arch wire through the brackets when required.

As indicated in U.S. Pat. No. 4,424,033, incorporated herein by reference in its entirety, one problem with the edgewise technique is that the rectangular arch wire tends to bind in the brackets secured to the posterior teeth as a result of excessive friction, and in some cases, the friction between the arch wire and the posterior tooth brackets interferes with the action of the arch wire in correcting anterior tooth protrusions. As a solution to this problem, U.S. Pat. No. 4,424,033 discloses an orthodontic arch wire provided with posterior segments which each have a circular cross-section and an anterior segment which has a uniform non-circular cross-section substantially throughout its entire length. Because the circular posterior segments of the arch wire have a lesser tendency to bind in the posterior brackets, there is a reduced likelihood that friction between the posterior tooth brackets and the arch wire will interfere with the application of a rearward force to the anterior teeth. Furthermore, the non-circular cross-section of the anterior segment of the arch wire cooperates with the slots in the anterior brackets to ensure rearward translation of the anterior teeth rather than tipping.

U.S. Pat. No. 4,424,033 also discloses an improvement of the arch wire associated with the solution above wherein rather than using a rectangular arch wire, an arch wire having a tapered, symmetrical, trapezoidal cross-section in its anterior segment is utilized. (It should be noted that for the purposes of this application, the term symmetrical trapezoidal cross-section will be used to refer to trapezoidal cross-sections in which neither the upper nor the lower surfaces thereof are perpendicular or substantially perpendicular to the vertical surfaces of the trapezoidal cross-section. Likewise, the term symmetrical trapezoidal arch wire will be used to refer to orthodontic arch wires of which at least a portion thereof has a symmetrical trapezoidal cross-section as defined above). The tapered anterior segment of the arch wire cooperates with correspondingly tapered edgewise slots in the anterior tooth brackets. Also, the tapered anterior segment and tapered slots slide together easily but provide a tight enough fit so that torque can be applied through the arch wire to the brackets. Furthermore, the tapered anterior segment and tapered slot eliminate the need for extremely close manufacturing tolerances.

Although the trapezoidal arch wires described in U.S. Pat. No. 4,424,033 overcome some of the more notable problems associated with the use of rectangular arch wires, it is likely that some orthodontists, especially those who have been practicing for a significant number of years, will refrain from using the symmetrical trapezoidal arch wires because such arch wires have a noticeably different configuration from the standard rectangular arch wires to which they have been accustomed. More particularly, since many orthodontists are accustomed to using rectangular arch wires as means for correcting malocclusions, such orthodontists may be unwilling to try the improved symmetrical trapezoidal arch wires.

Furthermore, since many existing orthodontic brackets are of the type having rectangular arch wires slots, some orthodontists may be willing to continue using the rectangular arch wires rather than the symmetrical trapezoidal arch wires, even though they are aware of the advantages of the symmetrical trapezoidal arch wires, in situations where they have a surplus of rectangular-slot brackets in their possession, or where their patients have already been outfitted with a series of rectangular-slot brackets.

SUMMARY

Accordingly, it is an object of the present invention to provide an orthodontic arch wire having a configuration which is similar in appearance to the commonly used rectangular arch wire, thereby increasing the likelihood that it will be utilized by practicing orthodontists, but which provides many of the advantages associated with the symmetrical trapezoidal arch wire.

It is also an object of the present invention to provide an orthodontic appliance including a series of conventional rectangular-slot brackets through which an orthodontic arch wire having a non-rectangular cross-section can extend, thereby providing flexibility by allowing orthodontists to choose between any one of a number arch wire configurations which may be available to such orthodontists.

Another object of the present invention is to provide an orthodontic arch wire having a configuration similar to that of the commonly used rectangular arch wire and a bracket conforming to such similarly configured arch wire in order to provide a orthodontic appliance which, as a whole, is similar to t he conventional rectangular arch wire appliance, but which has many of the advantages previously yielded only by the symmetrical trapezoidal arch wire appliance.

In order to satisfy the objects, the present invention relates to the use of an orthodontic arch wire having a non-symmetrical trapezoidal cross-section in combination with a series of brackets having either rectangular slots or slots conforming to the non-symmetrical trapezoidal orthodontic arch wire. (It should be noted that for the purposes of this application, the term non-symmetrical trapezoidal cross-section will be used to refer to trapezoidal cross-sections in which on of the upper or the lower surfaces thereof is perpendicular or substantially perpendicular to the vertical surfaces of the trapezoidal cross-section, while the other is not. Likewise, the term non-symmetrical trapezoidal arch wire will be used to refer to orthodontic arch wires of which at least a portion thereof has a non-symmetrical trapezoidal cross-section as defined above). The present invention also relates to an orthodontic applicance including an orthodontic arch wire having a symmetrical trapezoidal cross-section in combination with a series of orthodontic brackets having rectangular slots.

Accordingly, the present invention is an orthodontic arch wire which is arch-shaped and which includes posterior segments and an anterior segment connecting the posterior segments, wherein: at least a portion of the arch wire has a uniform, non-circular cross-section substantially throughout its entire length; the uniform, non-circular cross-section of the arch wire portion has a first side which is substantially flat, a second side which is substantially flat and which converges towards the first side in the direction of an inner arch surface of the arch wire, and a pair of substantially flat, substantially vertical sides which connect the first and second sides and which form the inner arch surface of the arch wire and an outer arch surface of the arch wire, respectively; and at least the substantially vertical side forming the inner arch surface is substantially perpendicular with respect to the first side of the uniform, non-circular cross-section of the arch wire portion.

The present invention can also include an orthodontic arch wire bracket configured to be secured to the tooth of a patient, the bracket including at least three slot surfaces which form a bracket slot for supporting a portion of an orthodontic arch wire, wherein: the three slot surfaces include a first surface which is substantially flat, a second surface which is substantially flat, and a substantially flat, substantially vertical surface which connects the first and second surfaces; the second surface converges towards the first surface in the direction of the substantially vertical surface; and the substantially vertical surface is substantially perpendicular with respect to the first surface.

Additionally, the present invention can include an orthodontic appliance including a series of brackets configured to be secured to the teeth of the patient, the brackets having slots for supporting an orthodontic arch wire, and an orthodontic arch wire extending through the slots, wherein: the arch wire is arch-shaped and includes posterior segments and an anterior segment connecting the posterior segments; at least a portion of the arch wire has a uniform, non-circular cross-section substantially throughout its entire length; the uniform, non-circular cross-section of the arch wire portion has a first side which is substantially flat, a second side which is substantially flat and which converges towards the first side in the direction of an inner arch surface of the arch wire, and a pair of substantially flat, substantially vertical sides which connect the first and second sides and which form the inner arch surface of the arch wire and an outer arch surface of the arch wire, respectively; and at least the substantially vertical side forming the inner arch surface is substantially perpendicular with respect to the first side of the uniform, non-circular cross-section of the arch wire portion.

Finally, the present invention can include an orthodontic appliance including a series of brackets configured to be secured to the teeth of a patient, the brackets having slots for supporting an orthodontic arch wire, and an orthodontic arch wire extending through the slots, wherein: each of the slots is formed by at least three slot surfaces; the three slot surfaces include a first surface which is substantially flat, a second surface which is substantially flat, and a substantially flat, substantially vertical surface which connects the first and second surfaces; the first surface is substantially parallel with respect to the second surface; the vertical surface is substantially perpendicular with respect to the first and second surfaces; the arch wire is arch-shaped and includes posterior segments and an anterior segment connecting the posterior segments; the arch wire has a uniform, non-circular cross-section substantially throughout its entire length; the uniform, non-circular cross-section of the arch wire has a first side which is substantially flat, a second side which is substantially flat and which converges towards the first side in the direction of an inner arch surface of the arch wire, and a pair of substantially flat, substantially vertical sides which connect the first and second sides and which form the inner arch surface of the arch wire and an outer arch surface of the arch wire, respectively.

The advantages associated with the non-symmetrical trapezoidal arch wire of the present invention include a similarity in appearance to the conventional rectangular arch wire, which should alleviate apprehension on the part of orthodontists who have become accustomed to using the rectangular arch wire, and flexibility in mounting stemming from the ability of the non-symmetrical trapezoidal arch wire to fit into either rectangular-slot brackets or brackets conforming to the non-symmetrical trapezoidal arch wire. The non-symmetrical trapezoidal arch wire of the present invention also affords many of the advantages of the conventional symmetrical trapezoidal arch wire, such as ease in insertion, elimination of the need for close manufacturing tolerances, and the provision of a tight fit which allows the exertion of torque on the teeth. Finally, the advantage stemming from the use of a conventional symmetrical trapezoidal arch wire in combination with a series of conventional rectangular-slot orthodontic brackets is that orthodontists will no longer be limited to using rectangular-slot orthodontic brackets in combination with only rectangular orthodontic arch wires.

DETAILED DESCRIPTION OF EMBODIMENTS OF THE INVENTION

Figures 1, 2:
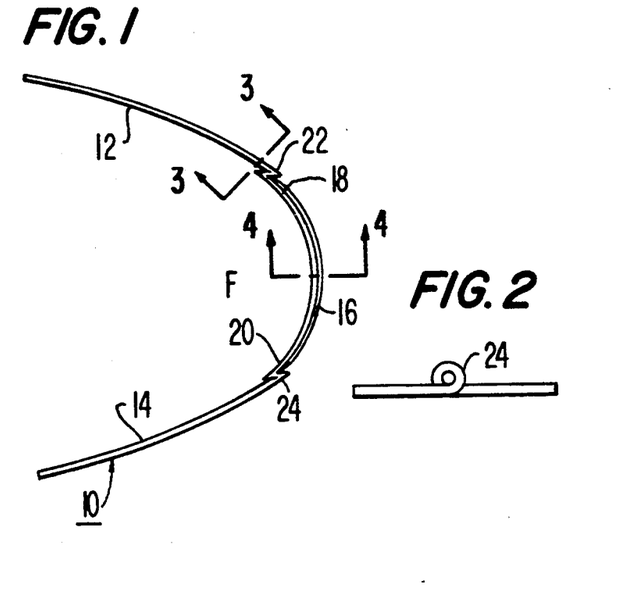
FIG. 1 is a top plan view of maxillary arch wire in accordance with the present invention.
FIG. 2 is a fragmentary elevational view of the arch wire of FIG. 1 showing a loop formed in the arch wire.

Arch wire 10, as shown in FIG. 1, is for use in the edgewise technique. It comprises posterior segments 12 and 14, and an anterior segment 16. The anterior segment extends the width of the anterior teeth, i.e., the central and lateral incisors. The transition points between the anterior and posterior segments are indicated at 18 and 20. Immediately behind these transitions, substantially at the proximal ends of the posterior segments, loops are formed at 22 and 24. These loops are for the purpose of attaching elastic to the arch wire. They may be formed in manufacture, or can be formed by the orthodontist himself. Loop 24 is shown, in side view, in FIG. 2.

Figure 3:
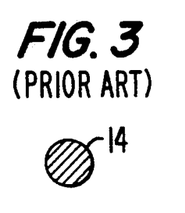
FIG. 3 is vertical section taken through a posterior portion of a conventional arch wire.
Figure 4:
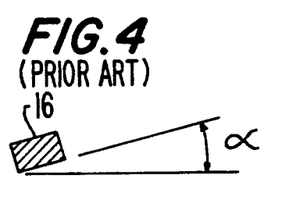
FIG. 4 is a vertical section taken through an anterior portion of a conventional arch wire.

In conventional orthodontic arch wires, the cross-section of the posterior segments is circular as shown in FIG. 3, while the anterior segment is rectangular as shown in FIG. 4. The rectangular anterior segment 16 may be torqued at an angle α Typically, the angle α ranges from 0° to 15°. The transition between the circular cross-sections and the rectangular cross-sections takes place immediately in front of the loops and approximately at the location of the transition points 18 and 20.

Figure 5:
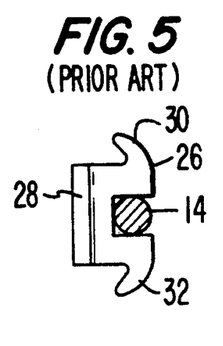
FIG. 5 is a side view of a posterior edgewise tooth bracket showing its relationship to the posterior segment of the arch wire of FIG. 3.

As shown in FIG. 5, posterior segment 14 of the arch wire is located in the rectangular slot of a posterior tooth bracket 26. This bracket is of conventional construction, having a base 28 for bonding to the tooth, and wings 30 and 32 for holding a ligature. It is possible for segment 14 of the arch wire to rotate within the slot of bracket 26. This possibility of rotation prevents binding from occurring, and allows the wire to slide smoothly in the slot of bracket 26 as rearward force is applied to the arch wire.

Figure 6:
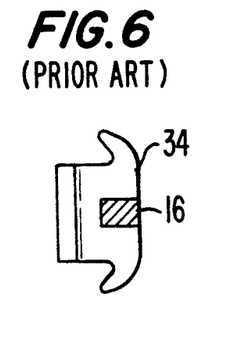
FIG. 6 is a side view of an anterior edgewise tooth bracket showing its relationship to the anterior segment of the arch wire of FIG. 4.

In FIG. 6, anterior segment 16 of the arch wire is shown in a slot in another conventional tooth bracket 34 similar in construction to bracket 26. The height of the anterior segment 16 of the arch wire is substantially equal to the height of the slot in bracket 34. This prevents relative rotation between the bracket and the arch wire. Since there can be no relative rotation, a rearward force applied by the arch wire to bracket 34 will cause the entire tooth to translate rearwardly instead of tipping inwardly.

Figure 7:
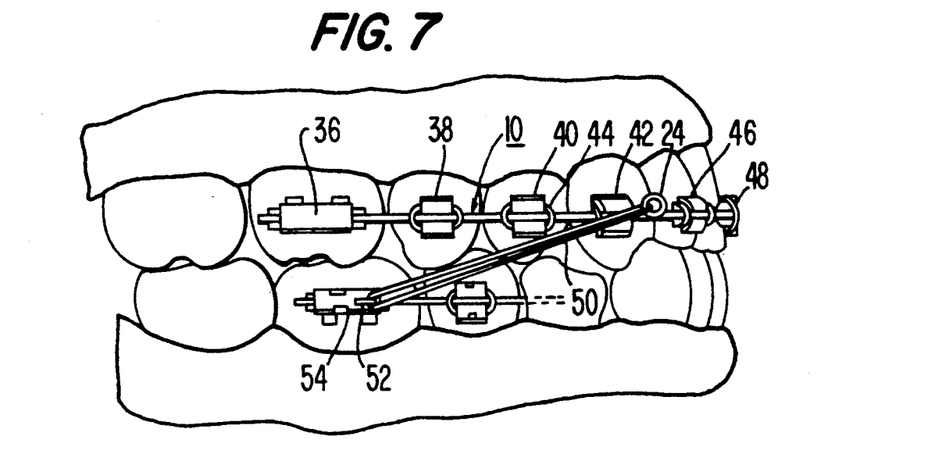
FIG. 7 is a fragmentary side elevation showing teeth of a typical patient with an arch wire in accordance with the present invention fitted in edgewise brackets on the maxillary teeth.

As shown in FIG. 7, the distal portion of posterior segment 14 of arch wire 10 extends through a buccal tube 36 on the upper first molar. From there the arch wire extends through a series of brackets 38, 40, 42, 46 and 48 respectively on the second and first bicuspids, the canine, and the lateral and central incisors on the right side of the mouth. The configuration on the left side of the mouth is similar.

The transition between the circular cross-section of the posterior segment 14 of the arch wire and the rectangular configuration of anterior segment 16 is located approximately at transition point 20 between the canine and the lateral incisor. Loop 24 is formed in the circular portion of the wire at a location immediately behind transition point 20, but in front of canine bracket 42. The transition can be at locations other than between the canine and the lateral incisor. For example, the transition can be between the lateral and central incisor. The transition and the loop can be spaced from each other if desired.

An advantage of the of the conventional arch wire having circular posterior segments and a rectangular anterior segment over arch wires which are rectangular throughout is that loops can be much more readily and satisfactorily formed in the circular portions of the arch wire having circular posterior segments than in the rectangular arch wires.

Loop 24 is connected through an elastic 50 to a cleat 52 on buccal tube 54 on a lower molar. Elastic 50 applies rearward force to arch wire 10, which in turn applies a rearwardly directed force to the anterior teeth. Since the anterior section 16 of the arch wire cannot rotate with respect to brackets 46 and 48, tipping of the incisors is prevented and proper rearward translation takes place.

While only part of the manidibular arch wire is shown in FIG. 7 it can also be configured in accordance with the circular posterior segments and a rectangular anterior segment.

The conventional arch wire having circular posterior segments and a rectangular anterior segment can be used with any of a large variety of standard brackets as well as with specially designed brackets.

Such arch wires can be provided with appropiate offset bends where necessary, and the anterior segment can be untorqued or torqued to any desired degree. Other forms of loops or other devices for applying rearward forces to the arch wires can be provided. For example, arch wires with closing loops located behind the canines are used to close gaps, especially in cases involving extractions. The closing loops exert a rearward force on the anterior teeth, and simultaneously exert a forward force on particular posterior teeth to which distal portions of the arch wire are fixed. In this case, elastic may not be needed since rearward force on the anterior teeth is supplied by the closing loops themselves.

Figure 8:
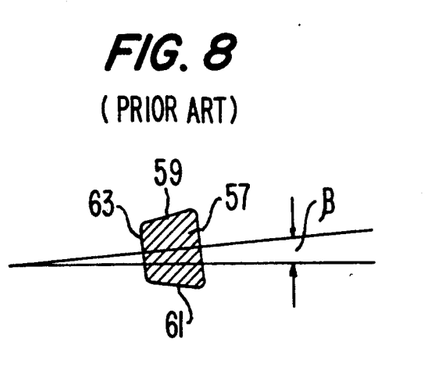
FIG. 8 is a vertical section taken through an anterior portion of a conventional arch wire.
Figure 9:
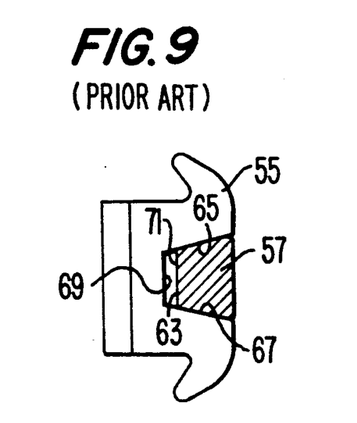
FIG. 9 is a side view of an anterior tooth bracket, showing its relationship to the anterior segment of the arch wire of FIG. 8.

The rectangular anterior arch wire segment shown in FIGS. 4 and 6 has an advantage in that it is usable with conventional rectangular-slot edgewise brackets. FIGS. 8 and 9 show a conventional yet less common alternative to the rectangular cross-sectional shape of the anterior arch wire segment in which the anterior segment of the arch wire is tapered and has a symmetrical trapezoidal cross-section. The conventional, tapered, anterior arch wire segment requires a special edgewise bracket having a tapered, non-rectangular slot, but it affords an advantage in that, compared to the rectangular arch wire, the tapered arch wire segment can be fitted to the brackets more easily while achieving a secure fit. The anterior portion 57 of the arch wire has a symmetrical trapezoidal cross-sectional shape with flat upper and lower surfaces 59 and 61 converging rearwardly toward the teeth of the patient. The rear edges of flat surfaces 59 and 61 are connected by a vertical surface 63.

Segment 57 is installed in a tapered edgewise slot of bracket 55. The slot has a flat upper surface 65, and a flat lower surface 67 facing surface 65. The surfaces cnverge toward the teeth of the patient and conform to surfaces 59 and 61 of the arch wire. The edges of surfaces 65 and 67 nearest the teeth are connected by vertical surface 69. Surfaces 63 and 69 are spaced from each other when the arch wire is fully installed in the slot to provide a small gap 71 which allows the arch wire to fit tightly in the slot. The horizontal dimension of gap 71 as shown in FIG. 8 can be very small, e.g., of the order of one-thousandth of an inch.

As shown in FIG. 8, the symmetrical trapezoidal anterior segment of the arch wire can be torqued at any desired torque angle $\beta$ so that when it is installed as shown in FIG. 9, it exerts a counterclockwise torque on the bracket. As the arch wire is pulled rearwardly by elastic or other means, the flat tapered surfaces come together into conforming relationship so that the arch wire can exert a torque on the bracket in the same manner as the arch wire of FIG. 4. Surfaces 59, 61, 65 and 67 are flat throughout substantial portions of their areas so that the arch wire and bracket are able to fit together in only one way. The angle between upper and lower surfaces 59 and 61 of the arch wire segment should be less than approximately 30 degrees. Angles substantially greater than 30 degrees unnecessarily reduce the available contact area between the arch wire segment and the bracket.

While the symmetrical trapezoidal cross-sectional shape is particularly suited to arch wires having circular posterior segments connected by a non-circular anterior segment, it is also applicable to an arch wire which has a uniform cross-section throughout its length. In the case of an arch wire which is uniform throughout, special brackets corresponding to the brackets shown in FIG. 9 are used on the posterior teeth as well as on the anterior teeth of the patient.

Whether the arch wire is symmetrically trapezoidal throughout, or symmetrically trapezoidal only throughout all or part of its anterior segment, the arch wire in accordance with FIGS. 8 and 9 is advantageous in that it enters the bracket slot more easily than a rectangular arch wire, and yet exerts torque just as effectively as the rectangular wire. The symmetrical trapezoidal wire is also advantageous because in the process of installation in the bracket, it adjusts its position automatically. The symmetrical trapezoidal wire is also advantageous in that it does not require the extremely close manufacturing tolerances needed for the rectangular arch wire and brackets.

Although the conventional, symmetrical trapezoidal arch wire shown in FIGS. 8 and 9 has advantages over the conventional yet more commonly used rectangular arch wire, orthodontists who are accustomed to using the rectangular arch wire may continue to do so due to their unfamiliarity with the newer but more effective symmetrical trapezoidal arch wire. Furthermore, since heretofore it has not been known to use the conventional, symmetrical trapezoidal arch wire in combination with conventional rectangular-slot orthodontic brackets, orthodontists who have a surplus of rectangular-slot brackets in their possession, or who have patients who have already been outfitted with rectangular-slot brackets, are left with no choice but to use rectangular arch wires even though they may be aware of the advantages of the symmetrical trapezoidal arch wires.

Figure 10:
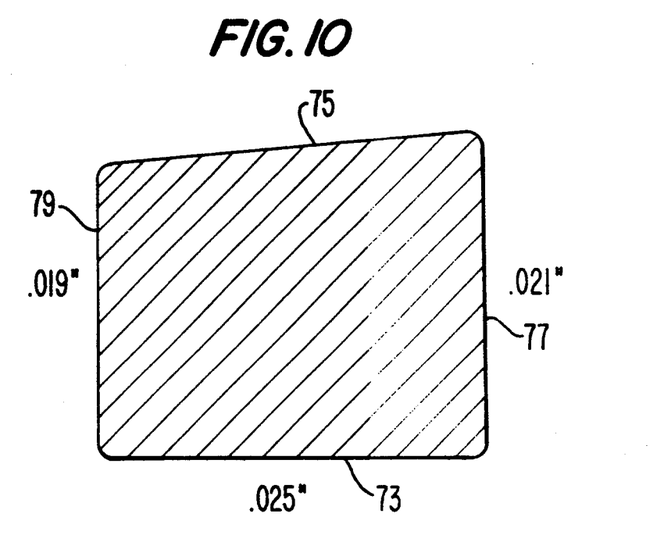
FIG. 10 is an enlarged vertical section taken through a portion of a non-symmetrical trapezoidal arch wire in accordance with the present invention, including dimensional designations.

An arch wire in accordance with the present invention having a non-symmetrical trapezoidal cross-section as shown in FIG. 10 provides a solution to such problems. Because the arch wire of the present invention is trapezoidal, it affords many of the advantages yielded by the symmetrical trapezoidal arch wires shown in FIGS. 8 and 9. Such advantages include facilitation in insertion due to the tapered configuration of the arch wire, the elimination of the need for close manufacturing tolerances, and the provision of a tight fit which allows the effective exertion of torque. Nevertheless, because the non-symmetrical arch wire of the present invention is somewhat similar in appearance to the commonly used rectangular arch wire, orthodontists who are familiar with the rectangular arch wire will have less apprehension in using the non-symmetrical trapezoidal arch wire. Furthermore, since the non-symmetrical trapezoidal arch wire of the present invention can be used in combination with brackets having either conforming slots or rectangular slots, flexibility in the types of arch wires which can be used by the orthodontist increases.

Figures 11, 12:
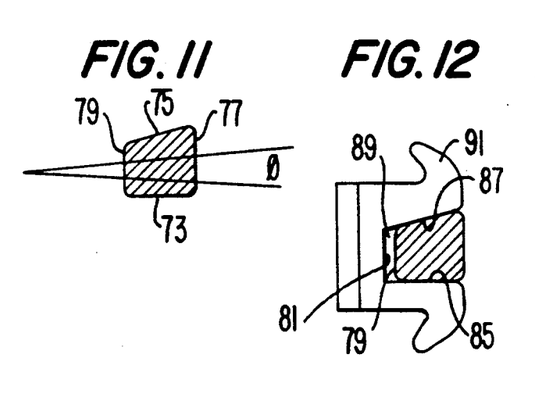
FIG. 11 is a reduced version of the vertical section of FIG. 10 with an increased upper surface slope.
FIG. 12 is a side view of a non-symmetrical trapezoidal-slot edgewise tooth bracket showing its relationship to the portion of the arch wire shown in FIG. 11.

As shown in FIGS. 10 and 11, the non-symmetrical trapezoidal arch wire of the present invention is characterized in that at least a portion thereof (such as the anterior segment) has a non-symmetrical trapezoidal cross-section, although both the anterior and posterior segments can have such a cross-section so that the non-symmetrical trapezoidal cross-section extends substantially throughout the length of the entire arch wire. The present invention envisions non-symmetrical orthodontic arch wires which are the same as the various trapezoidal orthodontic arch wires described in U.S. Pat. No. 4,424,033, incorporated herein by reference, except that in the present invention, the trapezoidal portions of such various trapezoidal orthodontic arch wires are non-symmetrical rather than symmetrical. Thus, for example, the present invention can include an orthodontic arch wire having a non-symmetrical trapezoidal anterior segment and circular posterior segments.

With reference to FIG. 10, the non-symmetrical trapezoidal arch wire of the present invention, or at least a non-symmetrical trapezoidal portion thereof, has flat upper and lower surfaces 75 and 73, respectively, which are peripherally connected via flat vertical surfaces 77 and 79. Vertical surfaces 77 and 79 are parallel or substantially parallel to each other, and lower surface 73 is perpendicular or substantially perpendicular to each of the vertical surfaces. Thus, the present invention could conceiveably include the situation wherein lower surface 73 is perpendicular to each of parallel vertical surfaces 77 and 79. Vertical surface 79 forms the inner arch surface of the non-symmetrical trapezoidal arch wire (i.e., the inner surface of the arch shape formed by the arch wire which faces the teeth after the arch wire has been mounted), while vertical surface 77 forms the outer arch surface of the wire. In order to be consistent throughout this application, in each of FIGS. 10-17(l), the vertical surfaces facing left will be considered to be inner arch surfaces, while the vertical surfaces facing right will be considered to be outer arch surfaces.

As shown in FIG. 10, upper surface 75 converges toward lower surface 73 in the direction of the inner arch surface or vertical surface 79. This slope of conversion, as can be seen by comparing FIGS. 10 and 11, can have any one of a number of values. Although not limited to the following dimensions, a typical arch wire of the type shown in FIG. 10 can have a width of 0.025 inch, with the height of inner arch surface 79 and the height of outer arch surface 77 being 0.019 inch and 0.021 inch, respectively.

In FIG. 12, the portion of the non-symmetrical trapezoidal arch wire having a non-symmetrical cross-section is shown extending through a slot in bracket 91. The slot has a flat upper surface 87, a flat lower surface 85 facing surface 87, and a vertical or substantially vertical surface 81. Upper surface 87 converges towards lower surface 85 in the direction of vertical surface 81 so that the upper and lower surfaces conform to surfaces 75 and 73 of the non-symmetrical trapezoidal section of the arch wire. The edges of surfaces 87 and 85 nearest the teeth are connected by vertical surface 81. Surfaces 79 and 81 are spaced from each other when the arch wire is fully installed in the slot to provide a small gap 89 which allows the arch wire to fit tightly in the slot. The horizontal dimension of gap 89 as shown FIG. 12 can be very small, e.g., of the order of one-thousandth of an inch, or nonexistent.

Figure 13:
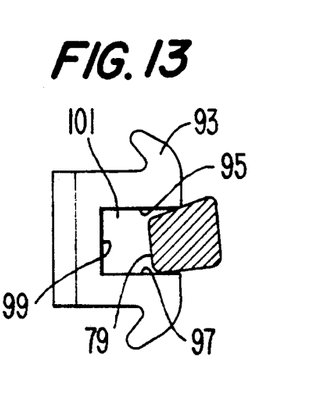
FIG. 13 is a side view of a rectangular-slot edgewise tooth bracket showing its relationship to the portion of the arch wire shown in FIG. 11.

As shown in FIG. 11, the segment of the arch wire having a non-symmetrical trapezoidal cross-section (such as the anterior segment) can be torqued at any desired angle $\phi$ so that when installed as shown in FIGS. 12 or 13, it exerts a torque on the bracket. As the arch wire is pulled rearwardly by elastic or other means, the flat tapered surfaces come together into conforming relationship so that the arch wire can exert a torque on the bracket in the same manner as does the arch wire of FIG. 4. Surfaces 73, 75, 85 and 87 should be flat throughout substantial portions of their areas so that the arch wire and bracket are able to fit together in only in one way.

While the non-symmetrical trapezoidal cross-sectional shape is particularly suited to arch wires having circular posterior segments connected by a non-circular anterior segment, it is also applicable to an arch wire which has a uniform cross-section throughout its length. In the case of an arch wire which is uniform throughout, special brackets corresponding to the bracket shown in FIG. 12 can be used on the posterior teeth as well as on the anterior teeth of the patient. Furthermore, the present invention, as can be seen by FIGS. 12 and 13, can be configured such that each portion of the orthodontic arch wire having a non-symmetrical trapezoidal cross-section can be fitted into either a rectangular-slot bracket or a bracket having a slots conforming to the non-symmetrical trapezoidal cross-section. Thus, the present invention could include an arch wire having a non-symmetrical trapezoidal cross-section throughout its entire length extending through a series of brackets including rectangular-slot brackets and brackets having slots conforming to the arch wire.

In FIG. 13, the non-symmetrical trapezoidal arch wire of the present invention is shown extending through a rectangular-slot bracket. The slot has a flat upper surface 95, a flat lower surface 97 facing surface 95, and a vertical or substantially vertical surface 99. Upper surface 95 and lower surface 97 are in parallel relation to each other, and perpendicular to vertical surface 99. The edges of surfaces 95 and 97 nearest the teeth are connected by vertical surface 99. Surfaces 79 and 99 are spaced from each other when the arch wire is fully installed in the slot to provide a gap 101 which allows the arch wire to fit tightly in the slot. Although the fit in FIG. 13 is not as tight as the fit provided by the conforming-slot bracket of FIG. 12, the embodiment of the present invention shown in FIG. 13 illustrates one of the advantages of the present invention, namely, the use of a trapezoidal arch wire in combination with an existing or conventional rectangular bracket. It should be noted that symmetrical trapezoidal arch wires, such as shown in FIGS. 8 and 9 or in U.S. Pat. No. 4,424,033, could also be used in combination with conventional rectangular brackets in the manner shown in FIG. 13. Thus, it is conceivable that a series of conventional rectangular-slot brackets could be used to support an arch wire having a symmetrical trapezoidal cross-section extending throughout its entire length. Furthermore, arch wires having a non-symmetrical trapezoidal cross-section throughout could also be used in combination with the rectangular-slot brackets as shown in FIG. 13. Likewise, arch wires having non-symmetrial trapezoidal anterior segments and circular posterior segments could also be used in combination with a series of rectangular brackets.

As with the embodiment shown in FIG. 12, the segment of the arch wire shown in FIG. 13 can be torqued at any desired angle $\phi$ so that when it is installed as shown, it exerts a torque on the bracket. As the arch wire is pulled rearwardly by elastic or other means, the flat tapered surfaces come together into conforming relationship so that the arch wire can exert a torque on the bracket in the same manner as does the arch wire of FIG. 4.

Figures 14, 15:
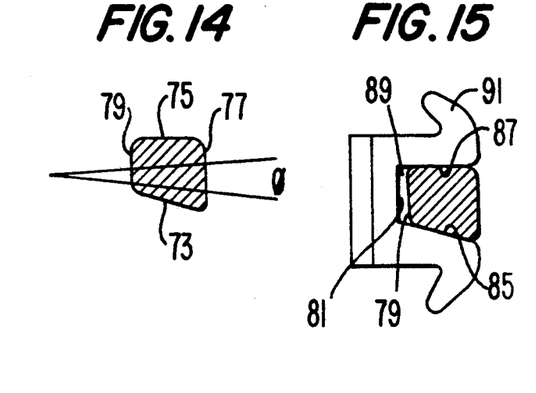
FIG. 14 is a vertical section taken through a portion of another non-symmetrical trapezoidal arch wire in accordance with the present invention.
FIG. 15 is a side view of a non-symmetrical trapezoidal-slot edgewise tooth bracket showing its relationship to the portion of the arch wire shown in FIG. 14.
Figure 16:
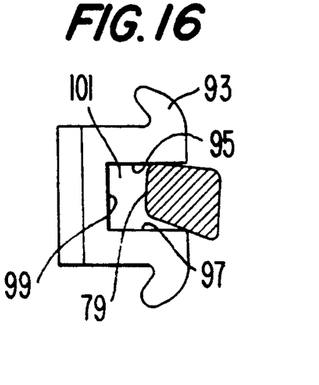
FIG. 16 is a side view of a rectangular-slot edgewise tooth bracket showing its relationship to the portion of the arc wire shown in FIG. 14.
Figure 17A:
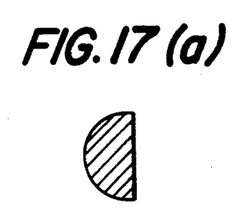
FIGS. 17(a)-17(l) are vertical sections taken through portions of various arch wires in accordance with the present invention.
Figure 17B:
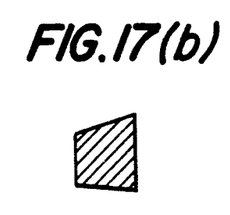
Figure 17C:
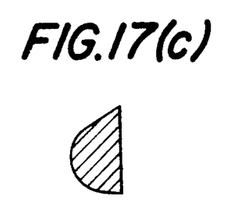
Figure 17D:
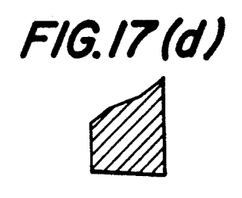
Figure 17E:
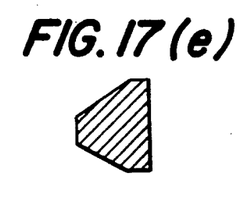
Figure 17F:
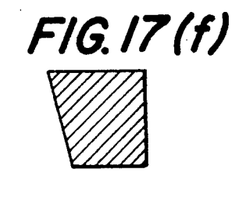
Figure 17G:
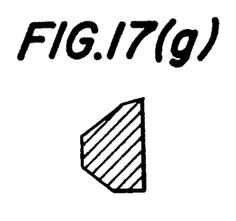
Figure 17H:
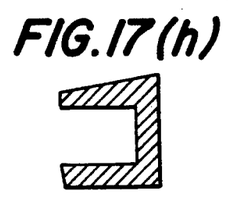
Figure 17I:
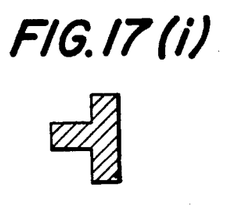
Figure 17J:
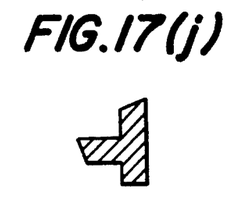
Figure 17K:
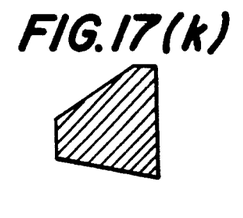
Figure 17L:
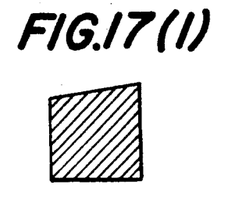

FIGS. 14-16 illustrate features of the present invention similar to those shown in FIGS. 11-13, respectively, except that rather than lower surface 73 being substantially perpendicular with respect to inner and outer arch surfaces 79 and 77, upper surface 75 is substantially perpendicular with respect to the inner and outer arch surfaces. Accordingly, the description of the invention above in connection with FIGS. 11-13 can essentially be applied to FIGS. 14-16, respectively, keeping in mind the difference between upper and lower surfaces 73 and 75 in these sets of figures.

FIGS. 17(a)-17(l) show various arch wire cross-sectional shapes that could be used with either rectangular-slot brackets, or brackets which respectively conform to such cross-sectional shapes. As can be seen by comparing FIGS. 10 and 17(l) for example, the arch wire of the present invention can have either rounded edges or substantially sharp corners.

The present invention, while retaining the advantages afforded by conventional symmetrical trapezoidal arch wires, is similar enough to the conventional but more commonly used rectangular arch wire that practicing orthodontists familar with the rectangular arch wire will not be apprehensive about its use. Furthermore, the present invention allows the application of advantages formerly associated only with trapezoidal arch wire appliances to orthodontic brackets having rectangular slots.

While the invention as been described in terms of its preferrred embodiments, it intended that numerous modifications may be made thereto without departing from the spirit and scope of the invention as defined in the appended claims.

I claim:

1. An orthodontic arch wire which is arch-shaped and which comprises posterior segments and an anterior segment connecting said posterior segments, wherein:
   at least one portion of said arch wire has a uniform, non-circular cross-section substantially throughout its entire length;
   said uniform, non-circular cross-section of said at least one arch wire portion has a first side which is substantially flat, a second side which is substantially flat and which converges towards said first side in the direction of an inner arch surface of said arch wire, and a pair of substantially flat, substantially vertical sides which connect said first and second sides and which form said inner arch surface of said arch wire and an outer arch surface of said arch wire, respectively; and
   at least the substantially vertical side forming said inner arch surface is substantially perpendicular with respect to said first side of said uniform, non-circular cross-section of said at least one arch wire portion.

2. An orthodontic arch wire according to claim 1, wherein said substantially vertical side of said uniform, non-circular cross-section which forms said outer arch surface is substantially perpendicular with respect to said first side and substantially parallel with respect to said substantially vertical side of said uniform, non-circular cross-section which forms said inner arch surface.

3. An orthodontic arch wire according to claim 2, wherein said at least one arch wire portion comprises said anterior segment.

4. An orthodontic arch wire according to claim 3, wherein each of said posterior segments has a uniform, non-circular cross-section substantially throughout its entire length.

5. An orthodontic arch wire according to claim 3, wherein said at least one arch wire portion comprises each of said posterior segments and said anterior segment so that said orthodontic arch wire has a single, uniform, non-circular cross-section substantially throughout its entire length.

6. An orthodontic arch wire bracket configured to be secured to the tooth of a patient, said bracket comprising at least three slot surfaces which form a bracket slot for supporting a portion of an orthodontic arch wire, wherein:
   said at least three slot surfaces comprise a first surface which is substantially flat, a second surface which is substantially flat, and a substantially flat, substantially vertical surface which connects said first and second surfaces;
   said second surface converges towards said first surface in the direction of said substantially vertical surface; and
   said substantially vertical surface is substantially perpendicular with respect to said first surface.

7. An orthodontic appliance comprising a series of brackets configured to be secured to the teeth of a patient, said brackets having slots for supporting an orthodontic arch wire, and an orthodontic arch wire extending through said slots, wherein:
   said arch wire is arch-shaped and comprises posterior segments and an anterior segment connecting said posterior segments;
   at least one portion of said arch wire has a uniform, non-circular cross-section substantially throughout its entire length;
   said uniform, non-circular cross-section of said at least one arch wire portion has a first side which is substantially flat, a second side which is substantially flat and which converges towards said first side in the direction of an inner arch surface of said arch wire, and a pair of substantially flat, substantially vertical sides which connect said first and second sides and which form said inner arch surface of said arch wire and an outer arch surface of said arch wire, respectively; and
   at least the substantially vertical side forming said inner arch surface is substantially perpendicular with respect to said first side of said uniform, non-circular cross-section of said at least one arch wire portion.

8. An orthodontic appliance according to claim 7, wherein said substantially vertical side of said uniform, non-circular cross-section which forms said outer arch surface is substantially perpendicular with respect to said first side and substantially parallel with respect to said substantially vertical side of said uniform, non-circular cross-section which forms said inner arch surface.

9. An orthodontic appliance according to claim 8, wherein:
   said at least one arch wire portion extends throught at least one of said slots;
   each one of said slots through which said at least one arch wire portion extends is formed by at least three slot surfaces;
   said at least three slot surfaces comprise a first surface which is substantially flat, a second surface which is substantially flat, and a substantially flat, substantially vertical surface which connects said first and second surfaces;
   said first surface is substantially parallel with respect to said second surface; and
   said vertical surface is substantially perpendicular with respect to said first and second surfaces.

10. An orthodontic appliance according to claim 8, wherein:
    said at least one arch wire portion extends through at least one of said slots;
    each one of said slots through which said at least one arch wire portion extends is formed by at least three slot surfaces;
    said at least three slot surfaces comprise a first surface which is substantially flat, a second surface which is substantially flat, and a substantially flat, substantially vertical surface which connects first and second surfaces;

said second surface converges towards said first surface in the direction of said substantially vertical surface; and said substantially vertical surface is substantially perpendicular with respect to said first surface.

11. An orthodontic appliance according to claim 10, wherein said at least one arch wire portion comprises said anterior segment.

12. An orthodontic appliance according to claim 11, wherein each of said posterior segments has a uniform, non-circular cross-section substantially throughout its entire length.

13. An orthodontic appliance according to claim 11, wherein said at least one arch wire portion comprises each of said posterior segments and said anterior segment so that said orthodontic arch wire has a single, uniform, non-circular cross-section substantially throughout its entire length.

14. An orthodontic appliance according to claim 13, wherein:

each of said slots through which said arch wire extends is formed by at least three slot surfaces;

said at least three slot surfaces comprise a first surface which is substantially flat, a second surface which is substantially flat, and a substantially flat, substantially vertical surface which connects first and second surfaces;

said second surface converges towards said first surface in the direction of s id substantially vertical surface; and said substantially vertical surface is substantially perpendicular with respect to said first surface.

15. An orthodontic appliance comprising a series of brackets configured to be secured to the teeth of a patient, said brackets having slots for supporting an orthodontic arch wire, and an orthodontic arch wire extending through said slots, wherein:

each of said slots is formed by at least three slot surfaces;

said at least three slots surfaces comprise a first surface which is substantially flat, a second surface which is substantially flat, and a substantially flat, substantially vertical surface which connects said first and second surfaces;

said first surface is substantially parallel with respect to said second surface;

said vertical surface is substantially perpendicular with respect to said first and second surfaces;

said arch wire is arch-shaped and comprises posterior segments and an anterior segment connecting said posterior segments;

said arch wire has a uniform, non-circular cross-section substantially throughout its entire length;

said uniform, non-circular cross-section of said arch wire has a first side which is substantially flat, a second side which is substantially flat and which converges towards said first side in the direction of an inner arch surface of said arch wire, and a pair of substantially flat, substantially vertical sides which connect said first and second sides and which form said inner arch surface of said arch wire and an outer arch surface of said arch wire, respectively.

* * * * *